(12) United States Patent
Kleitsch et al.

(10) Patent No.: US 7,866,617 B2
(45) Date of Patent: Jan. 11, 2011

(54) SLIDE AND LOCK CLAMPS

(75) Inventors: Andrew Kleitsch, Pewaukee, WI (US);
Michael Niemotka, Mundelein, IL (US);
Jesse Schultz, Lake Zurich, IL (US);
Daniel M. Terhune, Ingleslide, IL (US)

(73) Assignees: Baxter International Inc., Deerfield, IL (US); Baxter Healthcare S.A., Glattpark (Opfikon) (CH)

( * ) Notice: Subject to any disclaimer, the term of this patent is extended or adjusted under 35 U.S.C. 154(b) by 0 days.

(21) Appl. No.: 12/420,227

(22) Filed: Apr. 8, 2009

(65) Prior Publication Data
US 2010/0258690 A1 Oct. 14, 2010

(51) Int. Cl.
*F16B 1/00* (2006.01)

(52) U.S. Cl. .............. 248/230.3; 248/228.5; 248/230.5; 248/231.61; 269/6

(58) Field of Classification Search .............. 248/230.3, 248/121, 122.1, 226.11, 228.3, 228.5, 230.5, 248/231.41, 231.61, 230.2, 229.21, 229.22, 248/228.2, 229.24, 229.11, 229.12, 229.14, 248/231.31; 269/181, 43, 6
See application file for complete search history.

(56) References Cited

U.S. PATENT DOCUMENTS

| | | | |
|---|---|---|---|
| 904,485 A | 11/1908 | Johnson | |
| 1,359,775 A * | 11/1920 | White | 269/221 |
| 1,589,307 A | 6/1926 | Svebilius | |
| 2,452,849 A | 11/1948 | Gross | |
| 2,553,802 A * | 5/1951 | Woods | 269/142 |
| 2,584,955 A | 2/1952 | Williams | |
| 2,671,482 A | 3/1954 | Gordon | |
| 2,882,774 A | 4/1959 | Guttfeld | |
| 3,265,032 A | 8/1966 | Hume | |
| 3,570,836 A | 3/1971 | Pettavel | |
| 3,706,437 A | 12/1972 | Eberhardt | |
| 3,765,061 A | 10/1973 | Nash | |
| 3,878,757 A | 4/1975 | Puklus, Jr. | |
| 4,048,878 A | 9/1977 | Nystrom | |
| 4,134,499 A | 1/1979 | Joswig | |
| 4,217,847 A | 8/1980 | McCloud | |

(Continued)

FOREIGN PATENT DOCUMENTS

EP 0 185 877 7/1986

(Continued)

OTHER PUBLICATIONS

International Search Report, PCT/US2010/028590 mailed Aug. 23, 2010, 5 pages.

(Continued)

*Primary Examiner*—Anita M King
(74) *Attorney, Agent, or Firm*—K&L Gates LLP

(57) ABSTRACT

Slide and lock clamps for attaching to supports are provided. In a general embodiment, the present disclosure provides a clamp including a base plate comprising a first cradle. A rod is secured to the base plate. A sliding carriage is movably connected to the rod. The sliding carriage includes a lever, a cam, and a movable lock constructed and arranged for releasably locking the sliding carriage in place on the base plate. A second cradle is movably connected to the rod and positioned next to the sliding carriage for securing a support between the second cradle and the first cradle.

20 Claims, 5 Drawing Sheets

U.S. PATENT DOCUMENTS

| | | | |
|---|---|---|---|
| 4,674,722 A | 6/1987 | Danby et al. | |
| 4,702,448 A | 10/1987 | LoJacono et al. | |
| 4,706,963 A | 11/1987 | Geuss | |
| 4,729,535 A | 3/1988 | Frazier et al. | |
| 4,832,299 A | 5/1989 | Gorton et al. | |
| 4,844,397 A | 7/1989 | Skakoon et al. | |
| 4,997,154 A | 3/1991 | Little | |
| 5,149,036 A | 9/1992 | Sheehan | |
| 5,169,106 A | 12/1992 | Rasmussen | |
| 5,174,533 A | 12/1992 | Pryor et al. | |
| 5,222,420 A * | 6/1993 | Sorensen et al. | 81/487 |
| 5,322,253 A | 6/1994 | Stevens | |
| 5,332,184 A | 7/1994 | Davis | |
| 5,561,890 A | 10/1996 | Rich | |
| 5,584,457 A * | 12/1996 | Fawcett | 248/229.1 |
| D382,471 S | 8/1997 | Neff | |
| 5,785,480 A | 7/1998 | Difeo | |
| 5,829,723 A | 11/1998 | Brunner et al. | |
| 5,868,538 A | 2/1999 | Rathbun | |
| 5,898,974 A | 5/1999 | Boyer | |
| 5,964,440 A | 10/1999 | An et al. | |
| 6,017,008 A | 1/2000 | Farley | |
| 6,024,350 A | 2/2000 | Price et al. | |
| 6,050,615 A | 4/2000 | Weinhold | |
| 6,105,212 A | 8/2000 | Wright | |
| 6,158,729 A | 12/2000 | Tsai | |
| 6,382,576 B1 | 5/2002 | Heimbrock | |
| 6,474,632 B1 * | 11/2002 | Liou | 269/6 |
| 6,523,799 B2 | 2/2003 | Su | |
| 6,585,243 B1 | 7/2003 | Li | |
| 6,896,232 B2 | 5/2005 | Crowell et al. | |
| 6,964,425 B2 | 11/2005 | Turner | |
| 7,036,807 B1 * | 5/2006 | Gasparyan et al. | 269/181 |
| 7,073,755 B2 | 7/2006 | Michaud et al. | |
| 7,272,878 B2 | 9/2007 | Dixon | |
| 7,566,038 B2 * | 7/2009 | Scott et al. | 248/231.61 |
| 2006/0278785 A1 | 12/2006 | Wiesner et al. | |
| 2008/0077078 A1 | 3/2008 | Locke et al. | |

FOREIGN PATENT DOCUMENTS

| | | |
|---|---|---|
| GB | 2 232 192 | 12/1990 |
| WO | 2008153985 | 12/2008 |

OTHER PUBLICATIONS

Written Opinion of the International Searching Authority mailed Aug. 23, 2010, 9 pages.

* cited by examiner

SLIDE AND LOCK CLAMPS

BACKGROUND

The present disclosure is in the general field of clamps for securing objects to supporting poles, and in particular, for supporting medical devices connected to a patient on a supporting structure or pole.

One of the more basic tools used in a medical environment is an intravenous ("IV") stand. The typical IV stand includes an elongated member, or pole, that may be oriented either vertically or horizontally, and may additionally have any one of a variety of cross-sectional geometric shapes, including round, hexagonal, or square. The pole is placed upon and supported by a pedestal. Typically, IV devices such as supply bags or bottles of an IV liquid—normally blood, saline solution, or medication—are attached to the IV pole. These liquids are then delivered via a thin tube to a patient who is in a bed adjacent the IV stand.

As medical technologies and treatment techniques have advanced, the number of different IV liquids that are delivered to a patient has increased. As such, there are often additional devices that must be attached to the IV stand to manage, control, measure, and monitor the delivery of these various liquids. One such device is an infusion pump. In some situations, there may be more than one infusion pump, and there may be a controller or microcontroller that controls the infusion pumps. These devices are designed to attach to an IV stand, such as an IV pole, and allow for the attachment of numerous other devices in a collective and orderly fashion.

To minimize equipment costs and increase flexibility of use, these devices are typically required to be adaptable for use with various types of IV stands and poles. To accomplish this, such devices have typically been mounted on an IV pole by way of a clamping assembly. However, there are several disadvantages inherent in the currently available clamping assemblies. These clamping assemblies are sometimes capable of attachment to the IV stand in only one position. Thus, they may not be used interchangeably between a horizontally disposed IV pole and a vertically disposed IV pole.

Some clamping assemblies are limited as to the size or shape, or both, of the IV pole to which they can attach. While a clamp on a clamping assembly may be capable of attaching to a round IV pole, it may not be capable of attaching to a hexagonal or square shaped pole. Some clamps are limited to specific widths or diameters of poles to which they can properly attach. Each of these limitations restricts the adaptability and limits the usefulness of the clamping assembly.

An additional drawback is the effort required for positioning the clamp on a pole or repositioning the clamp on the same pole or on a different pole. Some clamps require two hands for positioning or repositioning the clamp, one hand for unlocking the clamp and another hand for moving or repositioning the clamp. Other clamps require an extended amount of time and effort to manually attach the medical device to the pole. Quick timing may be important in administering a prescribed medication, and time spent to attach or disattach an infusion pump from a pole could be crucial. In any case, it is desirable to make the movement and attachment of medical equipment for use easier and less time consuming.

SUMMARY

The present disclosure provides a quick-adjusting, quick-locking clamp that can be used to attach a medical device to a suitable support. For example, the clamp can be attached to IV poles, especially poles having a diameter from about 9.5 mm (0.375 in.) to about 38 mm (1.50 in.), although different embodiments may be used on poles of other diameters. While most IV poles are cylindrical, with a circular cross-section, the clamp may also be used on supports or poles with other peripheral shapes such as rectangular, square, or elliptical. The clamp is constructed and arranged to be adjusted and locked around the IV pole with a single hand.

In an embodiment, the present disclosure provides an IV pole clamp including a base plate having a first cradle, a rod secured to the base plate, and a sliding carriage movably connected to the rod. The sliding carriage further includes a lever, a cam, and a movable lock constructed and arranged for releasably locking the sliding carriage in place on the base plate. The clamp can further include a second cradle movably connected to the rod and positioned next to the slide carriage. The movable lock is mounted within the sliding carriage for movement by the cam and configured for clamping against the rod. In an embodiment, the rod can be a threaded rod secured in a groove defined by the base plate.

In one embodiment, the sliding carriage is secured to the rod by a bore defined by the sliding carriage that secures the rod. The cam is mounted on a pivot pin mounted in the sliding carriage, and the lever is attached to the cam. The clamp further includes a locking pin attached to the sliding carriage to prevent movement of the lever in a locked position. A portion of a surface of at least one of the stationary cradle and the sliding cradle includes a friction material.

A biasing mechanism can be inserted between an end cap of the base plate and the sliding carriage. The biasing mechanism is constructed and arranged to assist the user with moving the sliding carriage to a closed or locked position.

In another embodiment, the present disclosure provides a slide and lock clamp including a base plate having an end plate and a stationary cradle. The stationary cradle is configured to secure to one side of a support, such as a pole that is part of an intravenous stand. A rod is secured to the base plate. A sliding cradle is movably connected to the rod. The sliding cradle is configured to secure to an opposite side of the support. The clamp further includes a sliding carriage movably connected to the rod. A pivot pin is mounted within the sliding carriage. A cam is positioned in the sliding carriage and mounted on the pivot pin. A lever is attached to the cam, and a movable half-nut is mounted within the sliding carriage. The movable half-nut is configured to be moved by the cam and configured to be clamped against the rod. The end cap secures the rod to the base plate on at least one end of the base plate.

In another alternative embodiment, the present disclosure provides a slide-lock clamp including a base plate and a stationary cradle. The stationary cradle includes a first surface at an angle to the base plate and a second surface at about a right angle to the first surface. The stationary cradle is configured to secure one side of a cylindrical pole. A threaded rod is secured to the base plate. A sliding cradle is movably connected to the threaded rod. The sliding cradle includes a first portion at an angle to the base plate and a second portion at a steeper angle to the base plate. A sliding carriage is movably connected to the threaded rod. A pivot pin is secured to the sliding carriage. A cam is positioned within the sliding carriage and mounted on the pivot pin. A lever is connected to the cam, and a threaded half-nut is mounted within the sliding carriage. The threaded half-nut is configured to be moved by the cam and is also configured to be clamped against the threaded rod. The second portion includes an angled surface in a general shape of a V in one implementation.

In a further embodiment, the present disclosure provides a method of securing a medical device to a support such as, for example, a pole that is part of an intravenous stand. The method includes providing a clamp having (i) a base plate with a first cradle and a rod attached to the base plate, (ii) a sliding carriage movably connected to the rod, the sliding carriage having a lever, a cam, and a movable lock constructed and arranged to releasably lock the sliding carriage in place on the base plate, and (iii) a second cradle movably connected to the rod. The medical device is attached to the base plate of the clamp. The clamp is attached to the support so that the support is positioned between the first cradle and the second cradle. The sliding carriage is moved towards the support so that the first cradle and the second cradle are in contact with the support. Finally, the lever is adjusted so that the sliding carriage is locked in place on the base plate with the support firmly locked between the first cradle and the second cradle. The sliding carriage can be locked into a stationary position using a locking pin attached to the sliding carriage to prevent movement of the lever in a locked position.

It is accordingly an advantage of the present disclosure to provide an improved clamp for attaching medical devices to IV poles.

It is another advantage of the present disclosure to provide a quick adjusting clamp for quickly attaching a medical device to a pole.

It is yet another advantage of the present disclosure to provide a quick adjusting clamp for allowing a user to single-handedly attach a medical device to a pole.

Still further, it is an advantage of the present disclosure to provide a quick release clamp for quickly detaching a medical device from a pole.

Additional features and advantages are described herein, and will be apparent from the following Detailed Description and the figures.

DETAILED DESCRIPTION

Figure 1:
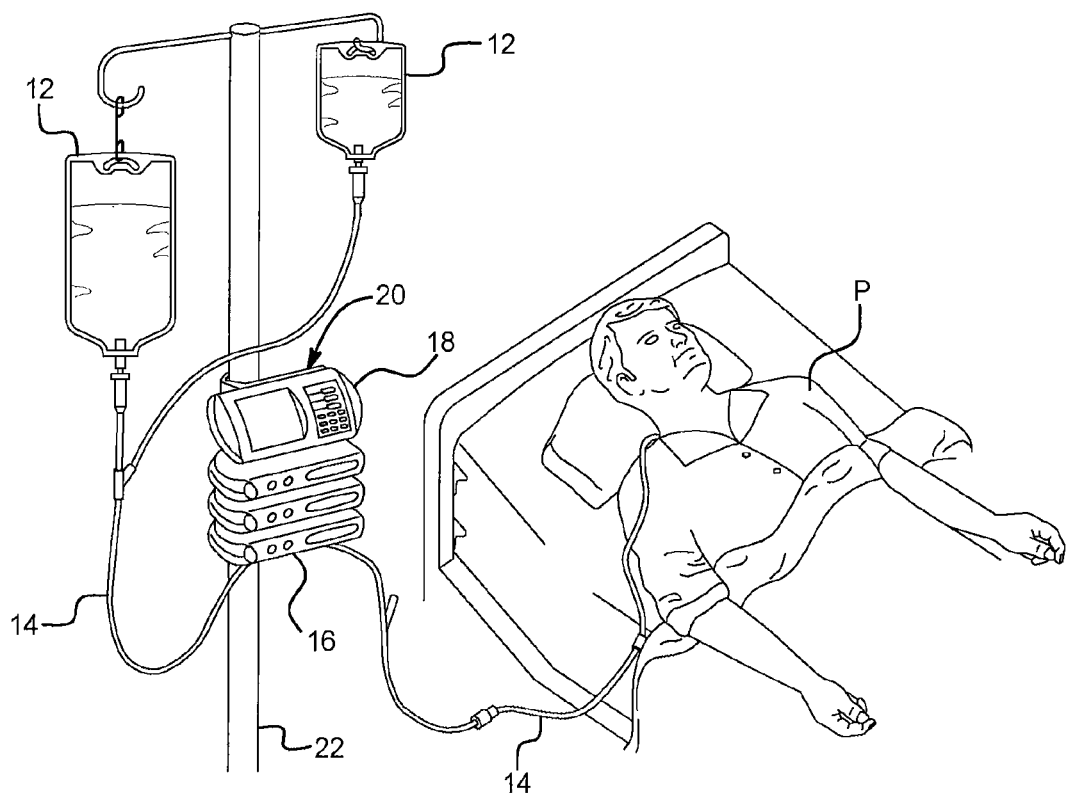
FIG. 1 is a perspective view of a slide and lock clamp in use on an IV pole in an embodiment of the present disclosure.

Referring now to the drawings and in particular to FIG. 1, a slide and lock clamp 20 in an embodiment of the present disclosure is illustrated. An intravenous system ("IV") 10 is shown for administering a medication to a patient P. The system 10 includes one or more containers 12 of an intravenous solution connected by tubing 14 to one or more infusion pumps 16 attached to and under the control of an infusion pump controller 18. Additional lengths of tubing 14 are provided to deliver the medication to the patient P. The back side of infusion pump controller 18 is attached to slide and lock clamp 20, which is then mounted on IV pole 22. The height of infusion pump 16 and infusion pump controller 18 can be adjustable to the desired position for the convenience of the patient and the caregiver that sets up pump 16 for delivering the medication to the patient P.

Figure 2:
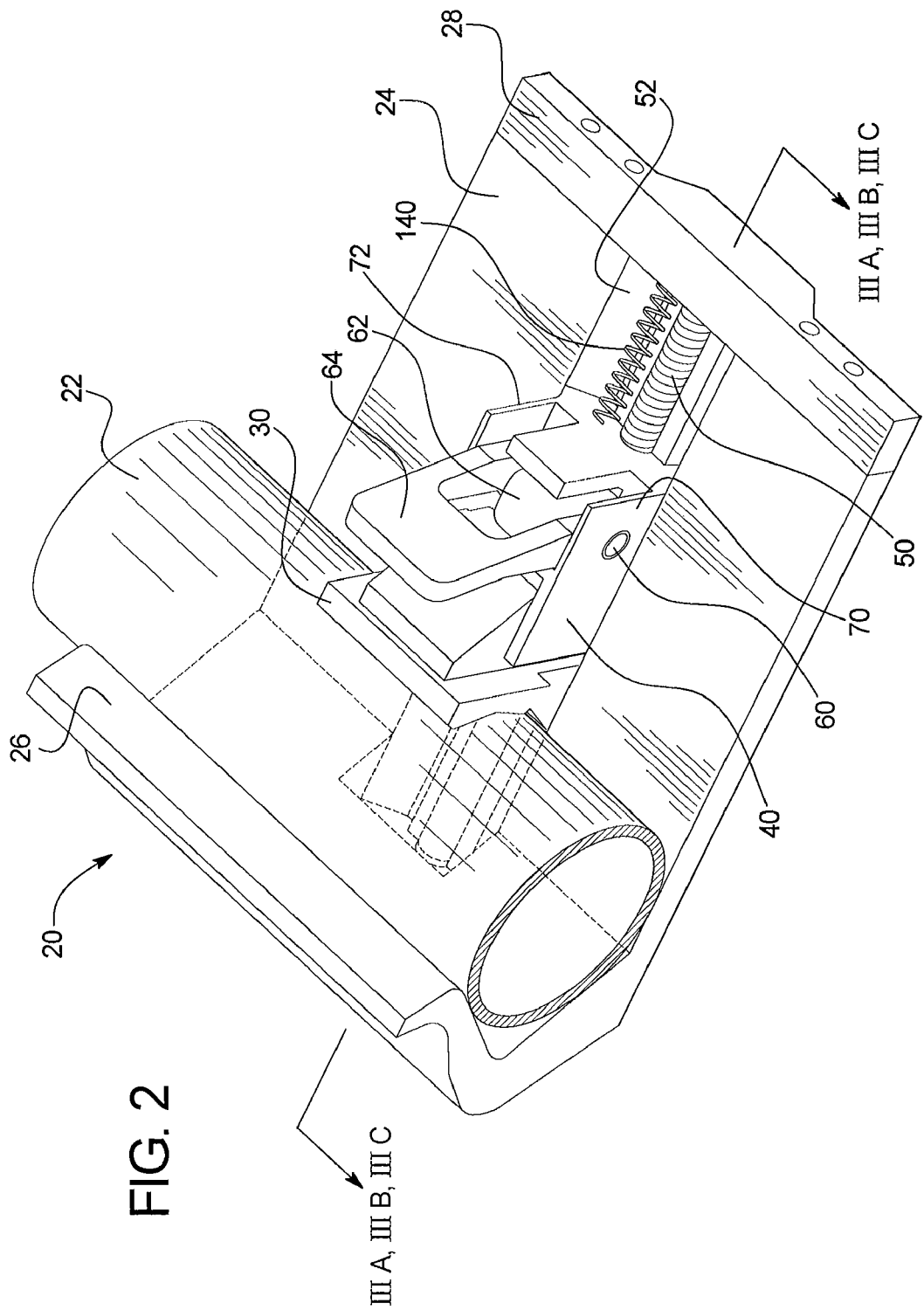
FIG. 2 is a perspective view of the clamp in a locked position surrounding the IV pole in an embodiment of the present disclosure.

FIG. 2 shows slide and lock clamp 20 in the locked position. The view of FIG. 2 depicts the side of clamp 20 that faces IV pole 22 and faces away from infusion pump 16. Clamp 20 includes a base plate 24 having a stationary cradle 26. Stationary cradle 26 is constructed and arranged to secure a portion of the circumference of IV pole 22. IV pole 22 is secured on the opposite circumferential portion by a movable or sliding cradle 30.

Threaded rod 50 is mounted to base plate 24 in a channel or groove 52. Rod 50 is secured on one end of base plate 24 to an end cap 28 attached to base plate 24. Rod 50 is secured on the other end of base plate 24 at the bottom portion of stationary cradle 26 (as seen in hidden line in FIG. 2.) For example, rod 50 can be secured within a bore 34, e.g., threaded, (FIGS. 3 to 5) defined by end plate 28 and a bore 36, e.g., smooth, defined by an end portion 32 of stationary cradle 26. Rod 50 could alternatively extend past one or both of end plate 28 and end portion 32, have threaded ends, and be held in place with one or more nuts tightened against plate 28 and/or portion 32. Rod 50 can have alternative cross-sectioned shapes, such as square, rectangular, trapezoidal, or other suitable polygonal shape. In an alternative embodiment, rod 50 does not have a threaded exterior surface.

As shown in FIGS. 2 to 5, sliding cradle 30 is movably or slideably attached to a sliding carriage 40. Sliding cradle 30 is mounted to an extended platform 42 that is part of sliding carriage 40. Cradle 30 slides with platform 42 of carriage 40, so that they collectively translate back and forth along rod 50. Sliding cradle 30 and sliding carriage 40 define bores (not shown) or upside down U-shaped channels (not shown) through their bottom portions through which rod 50 fits to retain sliding cradle 30 and sliding carriage 40 within groove 52 and prevent sliding cradle 30 and sliding carriage 40 from being removed from groove 52 and away from base plate 24.

As further illustrated in FIGS. 2 to 5, a pivot pin 60 is mounted within sliding carriage 40. A cam 62 is positioned in sliding carriage 40 and mounted on pivot pin 60. A lever 64 is attached to cam 62. A movable lock 66 is mounted within sliding carriage 40. Movable lock 66 is configured for movement by cam 62 and is positioned to clamp against rod 50, so as to lock cradle 30 and carriage 40 in place against IV pole 22.

More specifically, sliding carriage 40 acts as a housing for pivot pin 60 on which cam 62 is mounted. Pivot pin 60 is attached to sides 70 and 72 (FIG. 2) of sliding carriage 40. Cam 62 is connected to lever 64 so that when lever 64 is rotated by a user, cam 62 rotates as well. Cam 62 may be molded into lever 64 or may otherwise be integrally assembled with lever 64. Cam 62 pivots about pivot pin 60 as a user rotates lever 64 upward. This action also pushes down movable lock 66 onto rod 50 to lock sliding carriage 40 in place. Lever 64 can include a textured grip for a user to more easily grasp and rotate lever 64. Also, the bottom of lock 66 can be soft or rubberized to frictionally engage rod 50.

Figure 3:
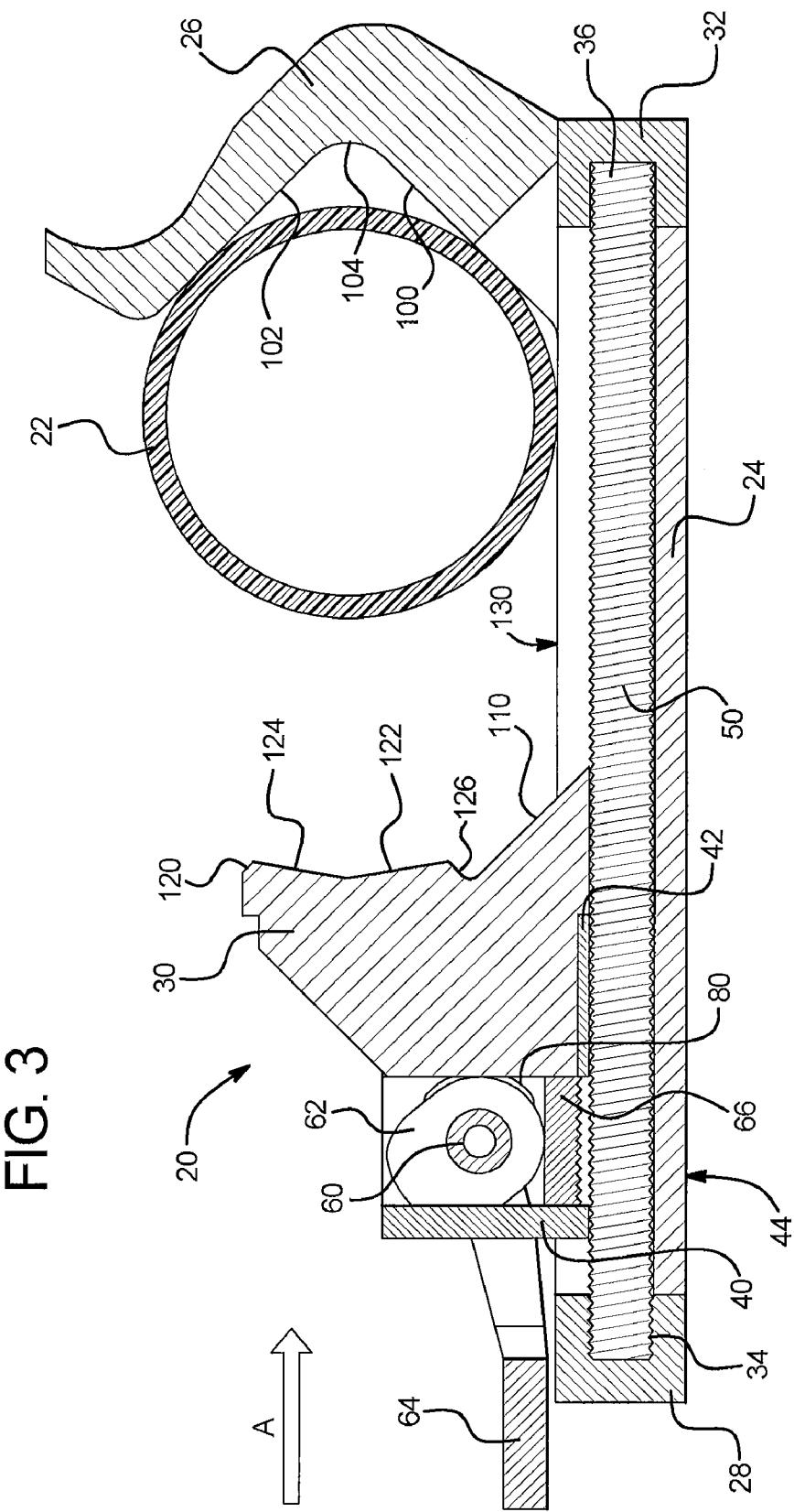
FIG. 3 is an elevation cross-section view of the clamp taken along line III-III in FIG. 2 in a released position.

Lock 66 may be a partially threaded half-nut or other suitable compression member that prevents movement of sliding carriage 40 when lock 66 is brought into contact with rod 50. When lock 66 is a half-nut, its threads are exposed and can engage with the threads of rod 50 in a locked position. Moving lever 64 clockwise rotates cam 62 clockwise, thereby pushing lock 66 downward towards rod 50 as described in more detail below. As illustrated in FIG. 3, a biasing mechanism 80 can be added to lock 66 to assist in pressing lock 66 firmly against cam 62.

As further illustrated in FIG. 3, in an embodiment, stationary cradle 26 and sliding cradle 30 are shaped to maximize the locking ability of clamp 20. As illustrated, stationary cradle 26 includes a first surface 100 extending at about a 45° angle from base plate 24. Stationary cradle 26 also includes a second surface 102 that meets first surface 100 at rounded corner 104. Surface 102 extends at about a 135° angle from base plate 24. Corner 104 is radiused, and in one embodiment, the radius is from about 0.6 cm (0.25 in.) to about 1.3 cm (0.5 in.). First surface 100 can be at an angle of about 30° to about 60° to base plate 24. As illustrated in FIG. 3, first surface 100 is at approximately a right angle to second surface 102 but can alternatively be from about 30° to 60° from surface 130 of base plate 24. First surface 100 can therefore extend at other angles with respect to second surface 102.

Sliding cradle 30 operates with stationary cradle 26 to securely capture IV pole 22 for mounting the infusion pump 16 and controller 18, as noted above in connection with FIG. 1. Sliding cradle 30 and/or stationary cradle 26 can be modified to accommodate differently shaped IV poles. In the illustrated embodiment, the working or clamping side of sliding cradle 30 includes a first angled surface 110, angled in this embodiment, at about a 135° angle from base plate 24. The working side also includes a second angled surface 120 including a first surface portion 122 and a second surface portion 124. Portions 122 and 124 meet at an angle of about 160° relative to each other, that is, almost at a straight line. Second angled surface 120 overall forms almost a right angle to base plate 24.

First and second angled surfaces 110 and 120 meet at radiused corner 126. It should be appreciated that in alternative embodiments, first and second angled surfaces 110 and 120 can meet at an angled corner. First angled surface 110 and corner 126 are positioned as shown so that they can easily capture an IV pole of various diameters, e.g., from about 1 cm (0.375 in.) to about 3.8 cm (1.5 in.). In one embodiment, corner 126 is positioned about 1.9 cm (0.75 in.) above the inner working surface 130 of base plate 24. This allows clamp 20 to capture an IV pole about two to three times the diameter between corner 126 and surface 130.

For the working side of sliding cradle 30, corner 126 can be positioned at about one quarter to about one-half the height above surface 130 of the largest diameter pole that is expected to be used with clamp 20. In one embodiment, if the largest diameter pole expected is about 3.8 cm (about 1.50 in.), corner 126 is about 0.75 cm to about 1.5 cm (about 0.29 in. to about 0.59 in.) above surface 130 of base plate 24. It should be appreciated that other radii, distances, and dimensions may be used for stationary cradle 26 and sliding cradle 30 in alternative embodiments.

Figure 4:
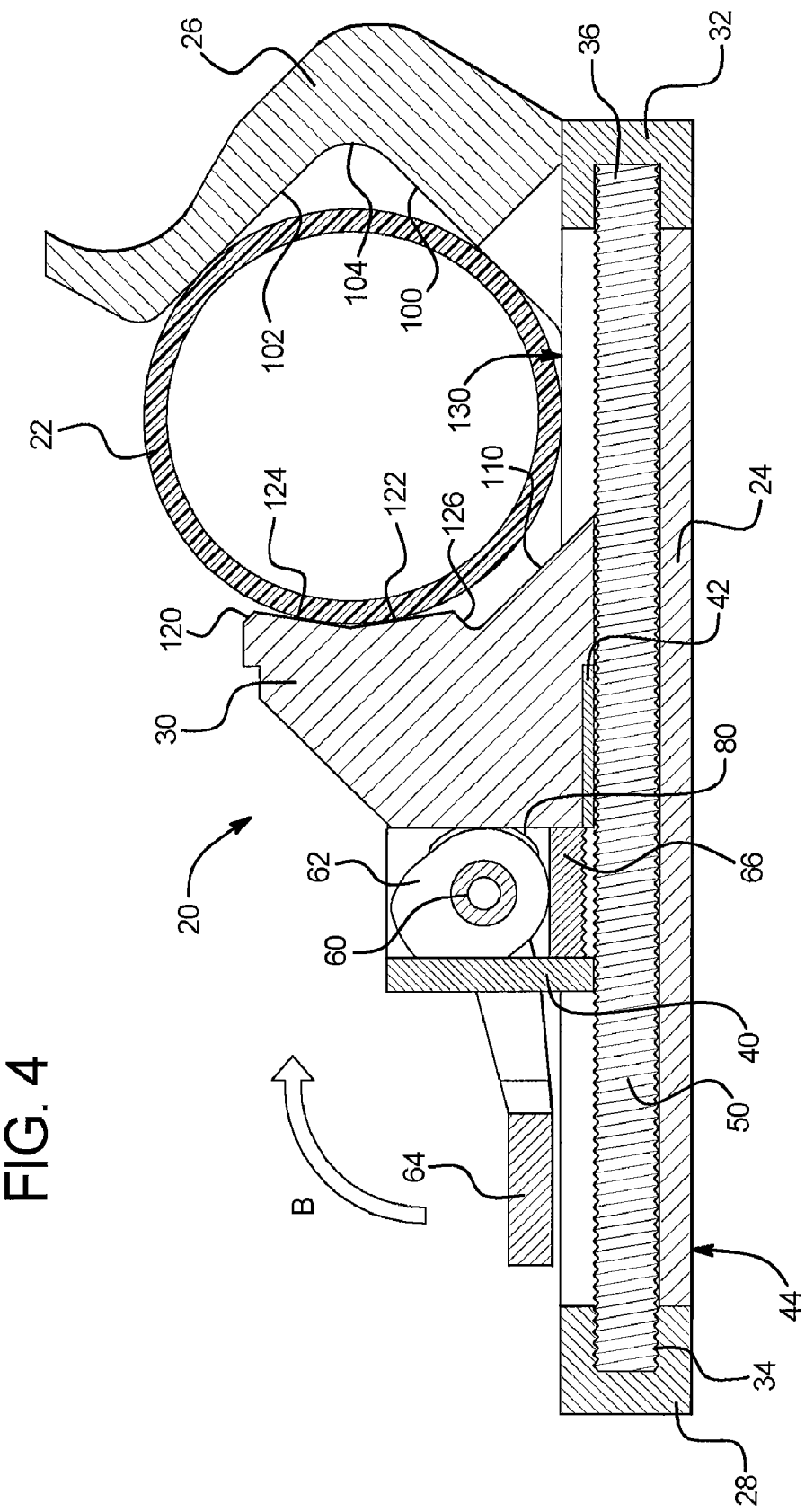
FIG. 4 is an elevation cross-section view of the clamp taken along line III-III in FIG. 2 illustrating the clamp in the released position engaging an IV pole.
Figure 5:
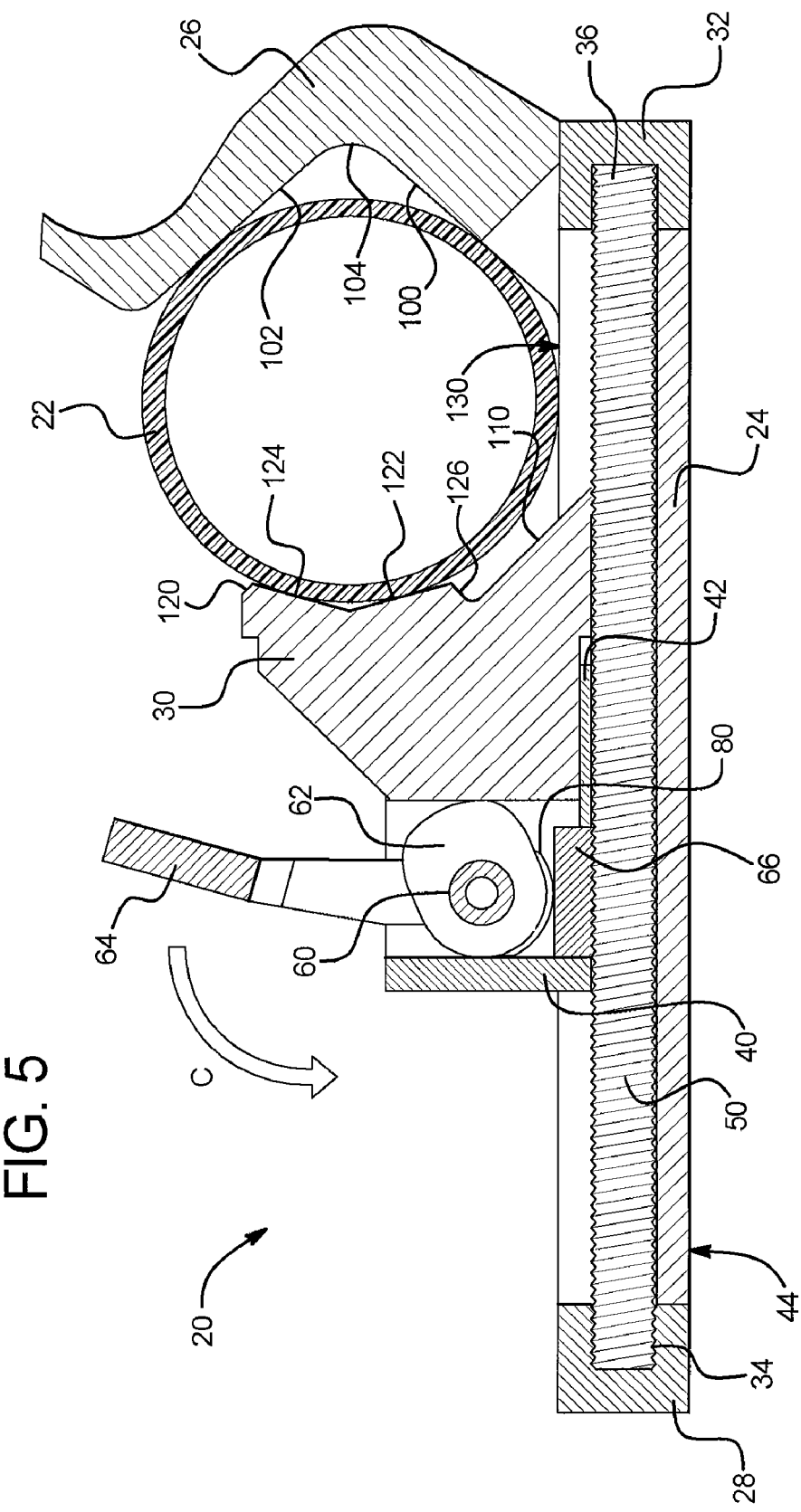
FIG. 5 is an elevation cross-section view of the clamp taken along line III-III in FIG. 2 illustrating the clamp in a locked position secured to the IV pole.

FIGS. 3-5 illustrate clamp 20 in alternative positions during operation of clamp 20. FIG. 3 shows clamp 20 in an open or released position, in which sliding cradle 30 and sliding carriage 40 are moved away from IV pole 22. During use, the user pushes carriage 40 to move sliding cradle 30 and sliding carriage 40 towards IV pole 22, as indicated by arrow A of FIG. 3. As sliding cradle 30 contacts IV pole 22, FIG. 4, first surface portion 122 and second surface portion 124 of sliding cradle 30 secure IV pole 22 on one side. First and second surfaces 100 and 102 of stationary cradle 26 secure IV pole 22 on its opposite side.

FIG. 5 illustrates clamp 20 in a closed or locked position on IV pole 22. Once clamp 20 is correctly positioned with respect to IV pole 22, the user then depresses or lifts lever 64 in an upward, clockwise direction, according to Arrow B shown in FIG. 4, which also rotates cam 62 on pivot pin 60. The movement of cam 62 causes lock 66 to move downward, towards rod 50, thereby compressing lock 66 against rod 50 as seen in FIG. 5. This prevents lock 66 from inadvertently moving along rod 50. At the same time, rotating cam 62 causes sliding cradle 30 to move away from sliding carriage 40 and further press against IV pole 22. This allows IV pole 22 to be securely and tightly locked between sliding cradle 30 and stationary cradle 26.

When the user wishes to remove clamp 20 from IV pole 22, lever 64 can be pressed towards base plate 24 according to arrow C in FIG. 5. Sliding carriage 40 and sliding cradle 30 can then be manually moved away from IV pole 22 to loosen the grip on IV pole 22 and allow clamp 22 to be removed from IV pole 22.

In an alternative embodiment, clamp 20 also includes a locking pin (not shown) that prevents movement of lever 64 once lever 64 is in the closed or locked position. The locking pin can be part of sliding carriage 40 or part of base plate 24 to prevent movement of lever 64 in a locked position. The locking pin can be constructed and arranged to require user interaction to release lever 64 to reduce the clamping force applied to IV pole 22 by clamp 20. This provides a safety mechanism to prevent clamp 20 from inadvertently becoming loose during its use.

In another alternative embodiment, a biasing mechanism 140 is inserted between end cap 28 and sliding carriage 40 as shown in FIG. 2 and is constructed and arranged to assist the user with moving sliding carriage 40 towards IV pole 22. For example, biasing mechanism 140 can become compressed as sliding carriage 40 moves closer to end cap 28. After the user moves sliding carriage 40 to the open position and inserts a support or rod between stationary cradle 26 and sliding cradle 30, biasing mechanism 140 will automatically move sliding carriage 40 back to the closed position without any effort by the user. The user can than lift lever 64 to tighten and completely secure the support or rod between stationary cradle 26 and sliding cradle 30.

As used herein, the term "biasing mechanism" includes mechanical springs and other compressible biasing elements, such as, compressible rubber or other elastomeric dome elements and solid compressible elastomeric bodies.

The side 44 of base plate 24 opposite of sliding carriage 40 can be removably or permanently attached to infusion pump controller 18 using any suitable attachment method. For example, base plate 24 can be attached to infusion pump controller 18 (or other devices) by one or more screws or fasteners. Alternatively, base plate 24 can be attached to infusion pump controller 18 (or other devices) using adhesives or welding techniques.

Clamp 20 and the various components of clamp 20 can be made using any suitable materials such as metals, polymers and plastics. Thus, clamp 20 can be designed to have a light weight, high strength, and durability.

It should be understood that various changes and modifications to the presently preferred embodiments described herein will be apparent to those skilled in the art. Such changes and modifications can be made without departing from the spirit and scope of the present subject matter and without diminishing its intended advantages. It is therefore intended that such changes and modifications be covered by the appended claims.

The invention claimed is:

1. An intravenous ("IV") pole clamp comprising:
   a base plate including a first cradle;
   a rod secured to the base plate;
   a sliding carriage movably connected to the rod, the sliding carriage comprising a lever, a cam, and a movable lock constructed and arranged for releasably locking the sliding carriage in place on the base plate when the first cradle and the carriage are in position to clamp to the IV pole, wherein the movable lock is mounted within the sliding carriage for movement by the cam and configured for clamping against the rod; and a second cradle movably connected to the rod and positioned adjacent to the sliding carriage.

2. The IV pole clamp of claim 1, wherein the movable lock is a threaded half-nut.

3. A slide and lock clamp comprising:
a base plate including a stationary cradle, the stationary cradle configured to secure to one side of a support;
a rod secured to the base plate;
a sliding cradle movably connected to the rod, the sliding cradle configured to secure to an opposite side of the support;
a sliding carriage movably connected to the rod;
a pivot pin mounted within the sliding carriage;
a cam positioned in the sliding carriage and mounted on the pivot pin;
a lever attached to the cam; and
a movable lock mounted within the sliding carriage, the movable lock configured to be moved by the cam and to be clamped against the rod.

4. The slide and lock clamp of claim 3, wherein the rod is at least one of cylindrical and threaded.

5. The slide and lock clamp of claim 3, wherein the rod is extended through the sliding cradle through a bore defined by the sliding cradle.

6. The slide and lock clamp of claim 3, wherein the stationary cradle comprises a first angled surface and a second angled surface to secure the support.

7. The slide and lock clamp of claim 3, wherein the support is a pole that is part of an intravenous stand.

8. An intravenous ("IV") pole clamp comprising:
a base plate including a stationary cradle;
a movable lock;
a first apparatus movable with respect to the base plate to position a movable cradle against an IV pole, wherein the IV pole is pressed against the stationary cradle, wherein the first apparatus is positioned adjacent to the movable cradle along the base plate; and
a second apparatus movable with respect to the movable cradle for further tightening of the movable cradle with respect to the stationary cradle, wherein the second apparatus includes a member rotatable to press the movable lock against a portion of the base plate.

9. The IV pole clamp of claim 8, wherein the member is a cam.

10. The IV pole clamp of claim 8, wherein the second apparatus, when moved to further tighten, is also configured to lock the second apparatus to the base plate.

11. An intravenous ("IV") pole clamp comprising:
a base plate including a cradle;
a rod secured to the base plate; and
a sliding carriage movably connected to the rod, the sliding carriage comprising a lever, a cam, and a movable lock constructed and arranged for releasably locking the sliding carriage in place on the base plate when the cradle and the carriage are in position to clamp to the IV pole, wherein the movable lock is mounted within the sliding carriage for movement by the cam and configured for clamping against the rod.

12. An intravenous ("IV") pole clamp comprising:
a base plate including a cradle;
a rod secured to the base plate; and
a sliding carriage movably connected to the rod, the sliding carriage comprising a lever, a cam, and a movable lock constructed and arranged for releasably locking the sliding carriage in place on the base plate when the cradle and the carriage are in position to clamp to the IV pole, wherein the movable lock is a threaded half-nut.

13. A slide and lock clamp comprising:
a base plate including a stationary cradle, the stationary cradle configured to secure to one side of a support;
a rod secured to the base plate;
a sliding cradle movably connected to the rod, the sliding cradle configured to secure to an opposite side of the support;
a sliding carriage movably connected to the rod;
a pivot pin mounted within the sliding carriage;
a cam positioned in the sliding carriage and mounted on the pivot pin;
a lever attached to the cam;
a movable lock mounted within the sliding carriage, the movable lock configured to be moved by the cam and to be clamped against the rod; and
a biasing mechanism attached to the movable lock and constructed and arranged to press against the cam.

14. A slide and lock clamp comprising:
a base plate including a stationary cradle, the stationary cradle configured to secure to one side of a support;
a rod secured to the base plate;
a sliding cradle movably connected to the rod, the sliding cradle configured to secure to an opposite side of the support;
a sliding carriage movably connected to the rod;
a pivot pin mounted within the sliding carriage;
a cam positioned in the sliding carriage and mounted on the pivot pin;
a lever attached to the cam; and
a movable lock mounted within the sliding carriage, the movable lock configured to be moved by the cam and to be clamped against the rod, wherein the movable lock is configured to move within a groove defined by the sliding carriage.

15. A slide and lock clamp comprising:
a base plate including a stationary cradle, the stationary cradle configured to secure to one side of a support;
a rod secured to the base plate, wherein the base plate includes an end cap that secures the rod to the base plate;
a sliding cradle movably connected to the rod, the sliding cradle configured to secure to an opposite side of the support;
a sliding carriage movably connected to the rod;
a pivot pin mounted within the sliding carriage;
a cam positioned in the sliding carriage and mounted on the pivot pin;
a lever attached to the cam; and
a movable lock mounted within the sliding carriage, the movable lock configured to be moved by the cam and to be clamped against the rod.

16. A slide and lock clamp comprising:
a base plate including a stationary cradle, the stationary cradle configured to secure to one side of a support;
a rod secured to the base plate;
a sliding cradle movably connected to the rod, the sliding cradle configured to secure to an opposite side of the support;
a sliding carriage movably connected to the rod;
a pivot pin mounted within the sliding carriage;
a cam positioned in the sliding carriage and mounted on the pivot pin;

a lever attached to the cam; and a movable lock mounted within the sliding carriage, the movable lock configured to be moved by the cam and to be clamped against the rod, wherein the rod is threaded and the lock is a half-nut that locks threadingly to the rod.

17. An intravenous ("IV") pole clamp comprising:

a base plate including a first cradle and defining a groove;

a rod secured to the base plate, wherein the rod is a threaded rod secured in the groove;

a sliding carriage movably connected to the rod, the sliding carriage including a lever, a cam, and a movable lock constructed and arranged for releasably locking the sliding carriage in place on the base plate when the first cradle and the carriage are in position to clamp to the IV pole; and a second cradle movably connected to the rod and positioned adjacent to the sliding carriage.

18. An intravenous ("IV") pole clamp comprising:

a base plate including a first cradle;

a rod secured to the base plate;

a sliding carriage movably connected to the rod, the sliding carriage including a lever, a cam, and a movable lock constructed and arranged for releasably locking the sliding carriage in place on the base plate when the first cradle and the carriage are in position to clamp to the IV pole, wherein the sliding carriage is secured to the rod by a bore defined by the sliding carriage that secures the rod; and a second cradle movably connected to the rod and positioned adjacent to the sliding carriage.

19. An intravenous ("IV") pole clamp comprising:

a base plate including a first cradle;

a rod secured to the base plate;

a sliding carriage movably connected to the rod, the sliding carriage including a lever, a cam, and a movable lock constructed and arranged for releasably locking the sliding carriage in place on the base plate when the first cradle and the carriage are in position to clamp to the IV pole, wherein the cam is mounted on a pivot pin mounted in the sliding carriage, and the lever is attached to the cam; and a second cradle movably connected to the rod and positioned adjacent to the sliding carriage.

20. An intravenous ("IV") pole clamp comprising:

a base plate including a stationary cradle;

a first apparatus movable with respect to the base plate to position a movable cradle against an IV pole, wherein the IV pole is pressed against the stationary cradle, wherein the first apparatus is positioned adjacent to the movable cradle along the base plate, and wherein the first apparatus includes a sliding carriage that is moved manually to position the movable cradle; and a second apparatus movable with respect to the movable cradle for further tightening of the movable cradle with respect to the stationary cradle.

\* \* \* \* \*